(12) United States Patent
In et al.

(10) Patent No.: US 12,007,574 B2
(45) Date of Patent: Jun. 11, 2024

(54) EYE DETECTION BASED SMART GLASSES DISPLAY DEVICE

(71) Applicant: MediThinQ Co., Ltd., Seongnam-si (KR)

(72) Inventors: Sungil In, Suwon-si (KR); Seungjoon Im, Seoul (KR)

(73) Assignee: MEDITHINQ CO., LTD., Seongnam-si (KR)

( * ) Notice: Subject to any disclaimer, the term of this patent is extended or adjusted under 35 U.S.C. 154(b) by 30 days.

(21) Appl. No.: 17/767,638

(22) PCT Filed: Oct. 12, 2020

(86) PCT No.: PCT/KR2020/013860
§ 371 (c)(1),
(2) Date: Apr. 8, 2022

(87) PCT Pub. No.: WO2021/071336
PCT Pub. Date: Apr. 15, 2021

(65) Prior Publication Data
US 2023/0258949 A1 Aug. 17, 2023

(30) Foreign Application Priority Data
Oct. 10, 2019 (KR) .................. 10-2019-0125456

(51) Int. Cl.
*G06F 3/01* (2006.01)
*G01C 3/02* (2006.01)
(Continued)

(52) U.S. Cl.
CPC ........... *G02B 27/0179* (2013.01); *G01C 3/02* (2013.01); *G02B 27/0172* (2013.01);
(Continued)

(58) Field of Classification Search
CPC ............ G02B 27/0179; G02B 27/0172; G02B 2027/0134; G02B 2027/0138;
(Continued)

(56) References Cited

U.S. PATENT DOCUMENTS 6,414,796 B1 * 7/2002 Muromachi ....... G02B 27/0101
359/589
2006/0176242 A1 8/2006 Jaramaz et al.
(Continued)

FOREIGN PATENT DOCUMENTS

JP 6-326946 A 11/1994
JP 2008-18015 A 1/2008
(Continued)

OTHER PUBLICATIONS

JP-2008-18015-A dated Jan. 31, 2008, Full Machine Translation is attached.

*Primary Examiner* — Rodney Amadiz
(74) *Attorney, Agent, or Firm* — Birch, Stewart, Kolasch & Birch, LLP (57) ABSTRACT

The present invention provides an eye detection based smart glasses display device including: a plurality of distance measurement units irradiating a laser to an eyeball including a fundus and measuring a first distance from the fundus and a second distance from a surface of the eyeball; an eye detection unit detecting an eye direction based on the first distance and the second distance; an image acquisition unit acquiring an overlay image; a screen synthesis unit recognizing an eye contact object within a predetermined range in the eye direction, and computing a location so as to display the overlay image at a designated location according to the eye contact object; and a display unit displaying the overlay image at the computed location and has a smart glasses type. Accordingly, according to the present invention, a display (Continued)

method and a display device which are capable of naturally displaying related information without disrupting an eye of a doctor.

17 Claims, 7 Drawing Sheets (51) Int. Cl.
*G02B 27/01* (2006.01)
*A61B 8/00* (2006.01)
*A61B 90/00* (2016.01)

(52) U.S. Cl.
CPC ............. *G06F 3/013* (2013.01); *A61B 8/462* (2013.01); *A61B 2090/061* (2016.02); *A61B 2090/365* (2016.02); *G02B 2027/0134* (2013.01); *G02B 2027/0138* (2013.01); *G02B 2027/014* (2013.01); *G02B 2027/0178* (2013.01); *G02B 2027/0187* (2013.01)

(58) Field of Classification Search
CPC ...... G02B 2027/014; G02B 2027/0178; G02B 2027/0187; G01C 3/02; G06F 3/013; A61B 8/462; A61B 2090/061; A61B 2090/365

See application file for complete search history.

(56) References Cited

U.S. PATENT DOCUMENTS

| | | | |
|---|---|---|---|
| 2011/0178784 A1* | 7/2011 | Sato | A61B 5/398 703/2 |
| 2011/0245670 A1* | 10/2011 | Tashiro | A61B 8/466 600/443 |
| 2012/0162549 A1* | 6/2012 | Gao | G02B 27/283 359/651 |
| 2014/0016092 A1* | 1/2014 | Chang | A61B 3/1005 351/246 |
| 2014/0168034 A1 | 6/2014 | Luebke et al. | |
| 2015/0103096 A1 | 4/2015 | Gotoda | |
| 2017/0205876 A1* | 7/2017 | Vidal | G01S 17/87 |
| 2017/0360412 A1* | 12/2017 | Rothberg | G06T 11/60 |
| 2018/0032136 A1 | 2/2018 | Kim et al. | |
| 2018/0239136 A1* | 8/2018 | Ishikawa | G06F 3/013 |
| 2019/0286229 A1 | 9/2019 | Chen et al. | |
| 2021/0373658 A1* | 12/2021 | Jeong | H04L 67/566 |
| 2023/0023425 A1* | 1/2023 | Suzuki | A61B 3/14 |

FOREIGN PATENT DOCUMENTS

| | | |
|---|---|---|
| JP | 2012-8290 A | 1/2012 |
| KR | 10-2015-0085710 A | 7/2015 |
| KR | 10-2097390 B1 | 4/2020 |
| WO | WO 2013/179427 A1 | 12/2013 |

\* cited by examiner

EYE DETECTION BASED SMART GLASSES DISPLAY DEVICE

CROSS REFERENCE TO RELATED APPLICATIONS

This application is the National Phase of PCT/KR2020/013860 filed on Oct. 12, 2020, which claims priority under 35 U.S.C. § 119(a) to Patent Application No. 10-2019-0125456 filed in the Republic of Korea on Oct. 10, 2019, all of which are hereby expressly incorporated by reference into the present application.

TECHNICAL FIELD

The present invention relates to an eye detection based smart glasses display device, and more particularly, to an eye detection based smart glasses display device, which detects an eye of a user and provides a natural overlay image through smart glasses according to an eye direction.

BACKGROUND ART

In recent years, as an application field of virtual reality ("VR"), augmented reality ("AR"), or mixed reality ("MR"), a medical service and a health care have been spotlighted. VR, AR, and MR technologies using smart glasses emerge as alternatives of promotion of medical experts and psychological treatment for coping with an increase in medical service demand such as an arrival of an aging era and psychological disease caused due to competition intensifying. In particular, the VR, the AR, and the MR deviate from a case where the VR is limitatively used for trauma treatment in related art and an application range of the VR, the AR, and the MR is extended to all medical areas such as surgery, treatment, rehabilitation, etc. When the VR, the AR, and the MR are used, training education is possible by implementing a virtual patient or organ, and a medical team may make an appropriate plan and perform a test in advance before surgery.

Since conventional medical equipment which does not use the VR, the AR, and the MR, e.g., an ultrasonic scanner should check an ultrasonic image to be displayed by a separate monitor screen, there is a problem in that a doctor should alternately check a patient and a monitor for treatment. Alternatively, there are many cases in which remote surgical equipment or robot surgical equipments cannot also efficiently show various information required for surgery to a medical team. Accordingly, there is a case where a head is turned to view the required information or the treatment should be performed by intuition of the doctor without the required information upon the surgery.

The problem and gaze dispersion serves as a factor which disrupts a concentration of the doctor upon diagnosis. In particular, if the concentration of the medical team is dispersed when a situation occurs in which a related information screen should be viewed during the diagnosis or surgery, the patient may be in danger or a part to be concentratively observed may also be lost.

Accordingly, a demand for a display method that can maximize the concentration of the doctor and maximally plan convenience of the medical team upon diagnosis by introducing the VR, the AR, and the MR into the conventional medical equipment is gradually increased.

Meanwhile, a technology which becomes a background of the present invention is prepared in order to facilitate understanding of the present invention. It should not be appreciated that matters disclosed in the technology which becomes the background of the present invention are present as prior art.

DISCLOSURE

Technical Problem

The present invention provides a revolutionary display method for preventing gaze dispersion of a doctor upon diagnosis by displaying an image a time and a point desired by the doctor through equipment such as AR, MR, VR, etc., in a medical device.

In particular, an object to be achieved by the present invention is to provide an eye detection based smart glasses display device, which displays an image or a video containing related information in a specific area which a user intuitively conveniently feels by detecting an eye of the user to allow the user to more accurately determine a diseased part or an inner part of a body of a patient through a virtual object.

The objects of the present invention are not limited to the aforementioned objects, and other objects, which are not mentioned above, will be apparent to a person having ordinary skill in the art from the following description.

Technical Solution

In order to solve the above-described problem, an eye detection based smart glasses display device according to an embodiment of the present invention may include: a plurality of distance measurement units irradiating a laser to an eyeball including a fundus and measuring a first distance from the fundus and a second distance from a surface of the eyeball; an eye detection unit detecting an eye direction based on the first distance and the second distance; an image acquisition unit acquiring an overlay image; a screen synthesis unit recognizing an eye contact object within a predetermined range in the eye direction, and computing a location so as to display the overlay image at a designated location according to the eye contact object; and a display unit displaying the overlay image at the computed location and has a smart glasses type.

In this case, the eye detection unit may sense a location of a pupil based on information on whether the distance measured by each of the plurality of distance measurement units being the first distance or the second distance.

In this case, the eye detection unit may detect the eye direction by sensing a direction which the pupil faces in the eyeball by the first distance measured by some distance measurement units among the plurality of distance measurement units.

Further, at least some of the plurality of distance measurement units may be arranged along a support supporting the display unit.

Further, the display unit may provide a screen including a circular guide area, and the screen synthesis unit may detect an eye direction of a user and acquire an eye correction reference value based on the eye direction detected along the guide area when an eye moves along the provided guide area.

Further, the eye correction reference value may include eccentricity, flatness, or a focal location of an ellipse.

Further, the screen synthesis unit may sense light irradiated by the eye contact object and extract a reference point for displaying the overlay image.

Further, the screen synthesis unit may extract a point spaced apart from the reference point by a predetermined interval as a screen boundary point.

Further, the display unit may display the overlay image in a 3D stereoscopic shape.

Further, the display unit may include a microdisplay, a lens, a panel, and a splitter.

Meanwhile, an eye detection based smart glasses display method according to the present invention may include: a distance measuring step of irradiating, by a plurality of distance measurement units, a laser to an eyeball including a fundus and measuring a first distance from the fundus and a second distance from a surface of the eyeball; an eye detecting step of detecting an eye direction based on the first distance and the second distance; an image acquiring step of acquiring an overlay image; a display location computing step of recognizing an eye contact object within a predetermined range in the eye direction, and computing a location so as to display the overlay image at a designated location according to the eye contact object; and a display step of displaying, by a display unit having a smart glasses type, the overlay image at the computed location.

In this case, in the eye detecting step, a location of a pupil may be sensed based on information on whether the distance measured by each of the plurality of distance measurement units being the first distance or the second distance.

In the eye detecting step, the eye direction may be detected by sensing a direction which the pupil faces in the eyeball by the first distance measured by some distance measurement units among the plurality of distance measurement units.

Further, the eye detection based smart glasses display method may further include: providing, by the display unit, a screen including a circular guide area; and detecting an eye direction of a user and acquiring an eye correction reference value based the eye direction detected along the guide area when the eye of the user moves along the provided guide area.

Further, the eye correction reference value may include eccentricity, flatness, or a focal location of an ellipse.

Further, the display location computing step may include sensing light irradiated by the eye contact object and extracting a reference point for displaying the overlay image.

Further, the display location computing step may further include extracting a point spaced apart from the reference point by a predetermined interval as a screen boundary point.

Further, the display step may include displaying the overlay image in a 3D stereoscopic shape.

Meanwhile, a computer readable recording medium according to an embodiment of the present invention may store instructions including: irradiating, by a plurality of distance measurement units, a laser to an eyeball including a fundus and measuring a first distance from the fundus and a second distance from a surface of the eyeball; detecting an eye direction based on the first distance and the second distance; acquiring an overlay image; recognizing an eye contact object within a predetermined range in the eye direction, and computing a location so as to display the overlay image at a designated location according to the eye contact object; and displaying, by a display unit having a smart glasses type, the overlay image at the computed location.

The solving means of the problem according to the present invention is not limited to the contents described above, and more various effects are included in the present specification.

Advantageous Effects

Basically, the present invention can provide a device which can display required information without dispersing an eye of a doctor at a time and a point desired by a doctor by using VR, AR, and MR.

According to the present invention, there is an effect that an augmented reality image which moves based on an eye motion is displayed in a specific area which the user intuitively conveniently feels to allow the user to concentratively determine a diseased part or an inner part of a body of a patient through a virtual object without gaze dispersion.

The effects according to the present invention are not limited by the contents exemplified above, and other various effects are included in the present specification.

BEST MODE

Advantages of the present invention, and methods for accomplishing the same will be more clearly understood from embodiments described in detail below with reference to the accompanying drawings. However, the present invention is not limited to the following embodiments but may be implemented in various different forms. The embodiments are provided only to make description of the present invention complete and to fully provide the scope of the present invention to a person having ordinary skill in the art to which the present invention pertains, and the present invention will be just defined by the appended claims.

The shapes, sizes, ratios, angles, numbers, and the like illustrated in the drawings for describing the embodiments of the present invention are merely examples, and the present invention is not limited thereto. Further, in describing the present invention, a detailed explanation of known related technologies may be omitted to avoid unnecessarily obscuring the subject matter of the present invention. The terms such as "including," "having," and "consisting of"

used herein are intended to allow other components to be added unless the terms are used with the term "only". Any references in a case where a component is expressed as a singular, the case includes plural unless expressly stated otherwise.

Components are interpreted to include an error range even if not expressly stated.

The features of various embodiments of the present invention can be partially or entirely bonded to or combined with each other and can be interlocked and operated in technically various ways to be sufficiently appreciated by those skilled in the art, and the embodiments can be carried out independently of or in association with each other.

Figure 1:
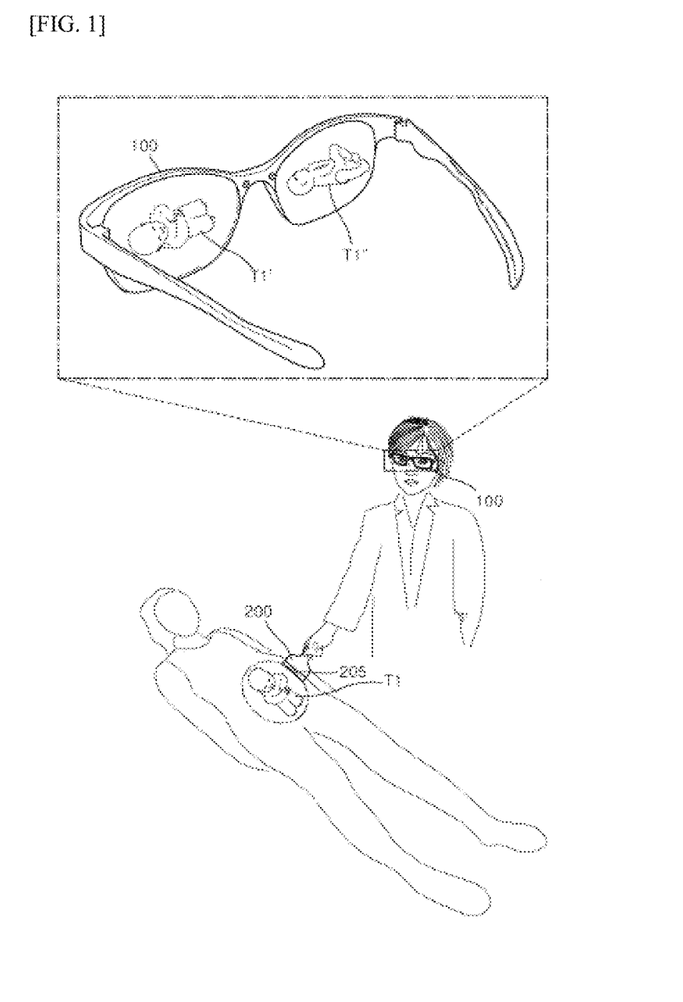
FIG. 1 is a diagram illustrating a display process of smart glasses according to an embodiment of the present invention.
Figure 2A:
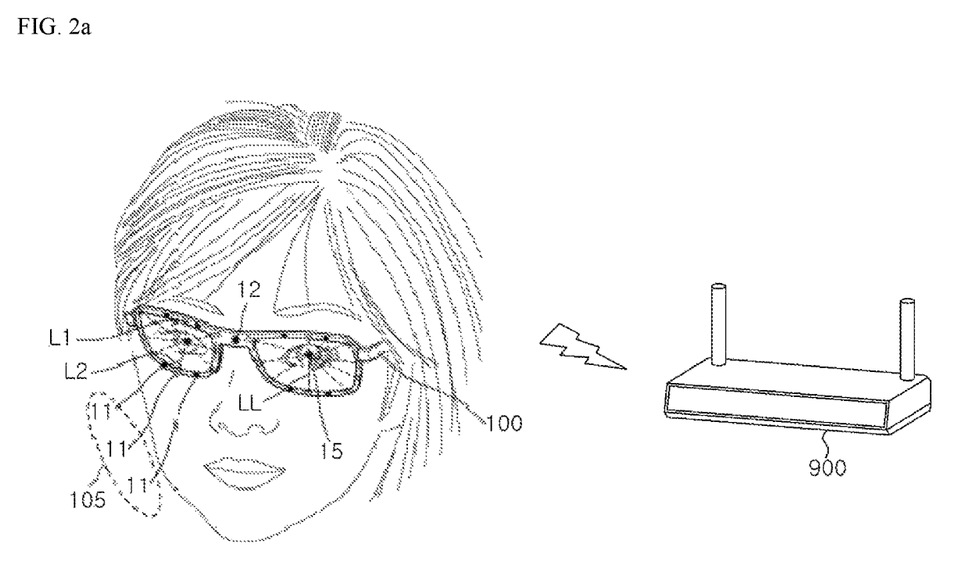
FIG. 2a is a schematic diagram of an eye detection based smart glasses display system according to an embodiment of the present invention.
Figure 2B:
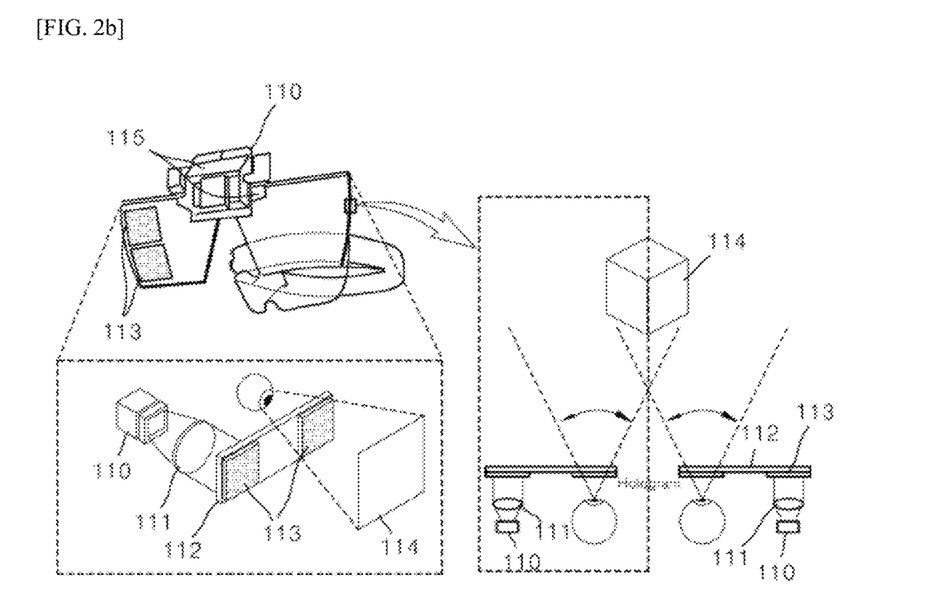
FIG. 2b is a configuration diagram of an eye detection based smart glasses display device according to an embodiment of the present invention.
Figure 2C:
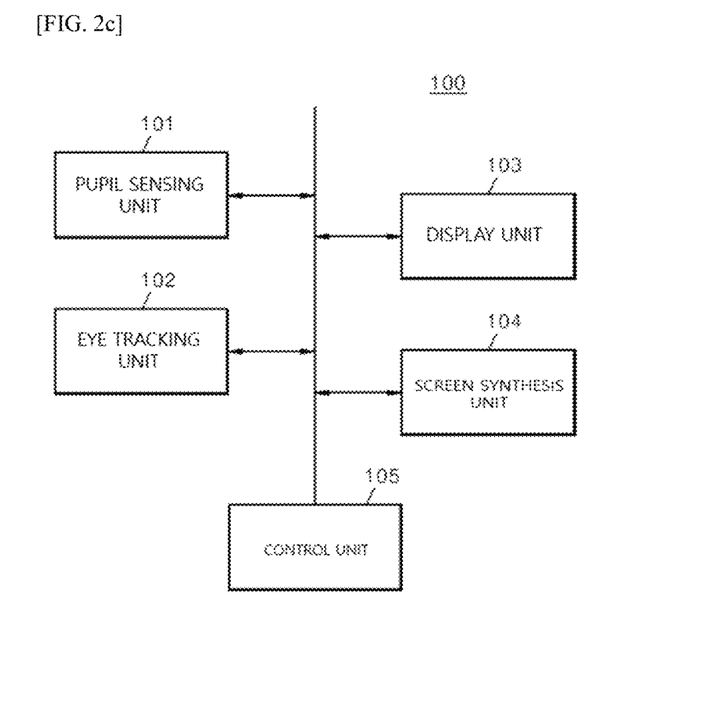
FIG. 2c is a block diagram of an eye detection based smart glasses display device according to an embodiment of the present invention.
Figure 3A:
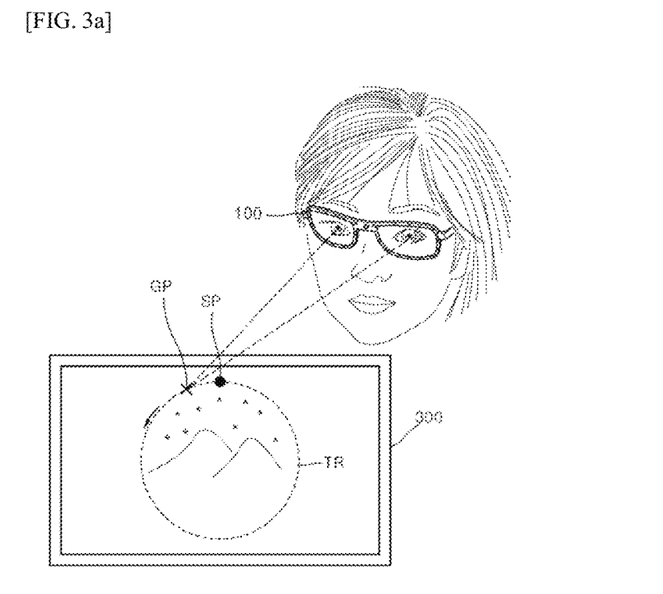
FIGS. 3a and 3b are diagrams for describing a calibration mode depending on eye detection according to an embodiment of the present invention.
Figure 3B:
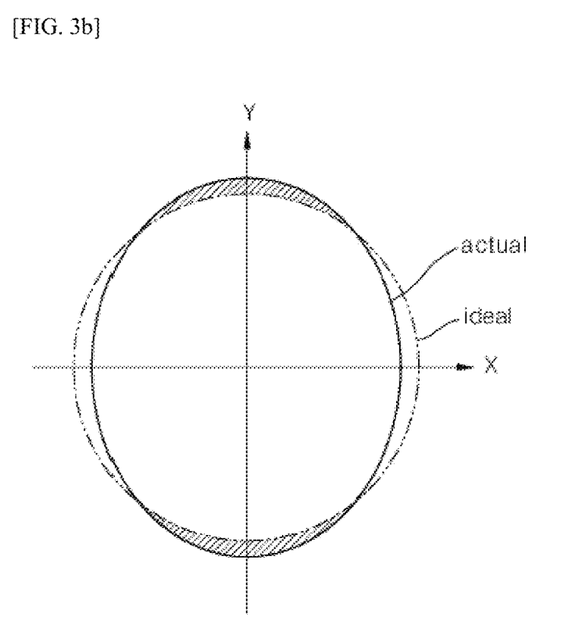
Figure 4:
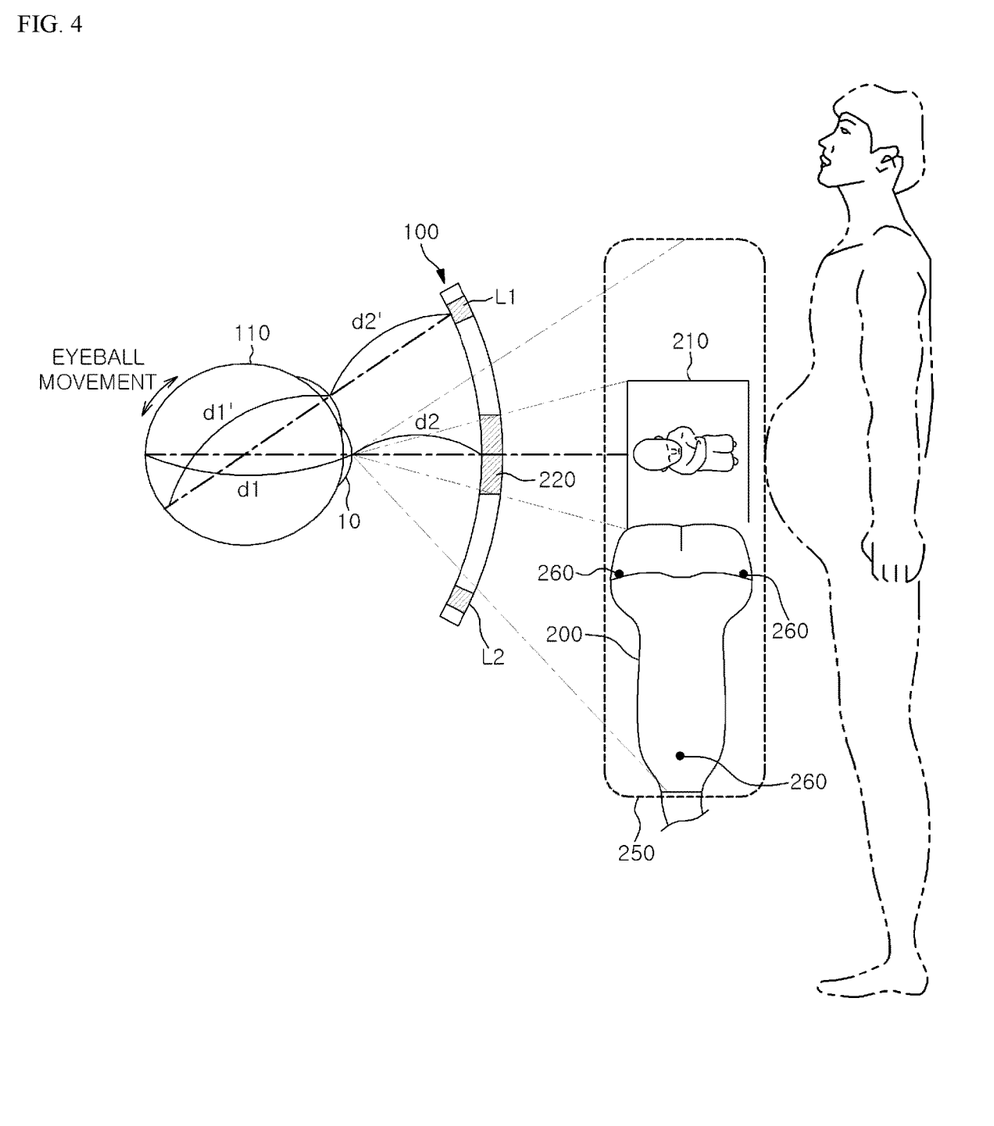
FIG. 4 is an exemplary diagram for describing a process of generating an image in a display according to an embodiment of the present invention.

FIG. 1 is an exemplary diagram illustrating an overlay image display process according to an embodiment of the present invention. FIG. 2a is a schematic diagram of an eye detection based augmented reality display system according to an embodiment of the present invention. FIG. 2b is a configuration diagram of an eye detection based smart glasses display device according to an embodiment of the present invention. FIG. 2c is a block diagram of an eye detection based smart glasses display device according to an embodiment of the present invention. FIGS. 3a and 3b are diagrams for describing eye direction correction depending on eye detection according to an embodiment of the present invention. FIG. 4 is a diagram for describing a process of displaying an overlay image in a display.

Referring to FIG. 1, an eye detection based smart glasses display system includes a smart glasses display device 100 based on eye detection, which displays an image or a video acquired from an image acquisition unit 205 in a specific area on a display depending on an eye contact object 200 as an overlay image or video of augmented reality, mixed reality, or virtual reality, and an eye detection server 900. However, in the embodiment of FIG. 1, a form in which the eye detection based smart glasses display device 100 and the eye detection server 900 are separated is illustrated, but the eye detection based smart glasses display device 100 and the eye detection server 900 may also be mounted on one housing. When the eye detection based smart glasses display device 100 and the eye detection server 900 are mounted on one housing, the eye detection based smart glasses display device 100 and the eye detection server 900 may be connected wiredly.

Further, in the embodiment, it is illustrated that the eye contact object 200 and the image acquisition unit 205 are implemented in one device as an ultrasonic scanner, but the eye contact object 200 and the image acquisition unit 205 may also be separate devices. For example, in a remote surgery robot, the eye contact object 200 may be a mes or a surgical site of a surgical patient. The image acquisition unit 205 may also be, for example, a unit that acquires an image displaying an area where the mes does not pass through a nerve of the surgical patient from an image stored in the eye detection server 900. In other words, the eye detection server 900 may store an image displaying the nerve of the patient based on a video photographed before the surgical patient is operated.

The eye detection based smart glasses display device 100 is a device that may detect the eye of the user by a plurality of distance measurement units 11 embedded therein, and display the image acquired by the image acquisition unit 205 on a screen of the display unit 103. Here, the smart glasses display device 100 recognizes the eye contact object 200, and then displays the video acquired by the image acquisition unit 205 in a preset area in relation to the recognized eye contact object 200. In this case, the eye contact object 200 may also be an electronic device or a general tool used for surgery, treatment, etc. For example, the eye contact object 200 may be the ultrasonic scanner, scissors, a clip, the mes, etc. In the embodiment, it is described that the eye contact object 200 is the ultrasonic scanner as a reference.

In the present invention, the eye detection based smart glasses display device 100 may be a scheme in which a screen 114 projected from a microdisplay 110 (see FIG. 2b) of the display unit 103 is reflected through both lenses 111, a panel 112, and a splitter 113, and shown to the eyes. Alternatively, the eye detection based smart glasses display device 100 may also be a form in which an external screen photographed through an external camera 12 of the smart glasses display device 100 or through a separate separated camera in a see-through mode while using an HMD display is shown while being overlapped with an overlay screen through a screen of the VR.

Referring to FIGS. 2a, 2b, and 2c, the eye detection based smart glasses display device 100 may include a pupil sensing unit 101, an eye detection unit 102, a display unit 103, a screen synthesis unit 104, and a control unit 105. In the pupil sensing unit 101, the eye detection unit 102, and the display unit 103, the screen synthesis unit 104 and the control unit 105 may be constituted by software, hardware, or a combination of the software and the hardware, and those skilled in the art may implement the components by using an appropriate means.

The pupil sensing unit 101 as a component that senses a pupil of the user includes a plurality of distance measurement units 11. In this case, the plurality of distance measurement units 11 may be arranged along a periphery of a glasses frame of the eye detection based smart glasses display device 100.

The distance measurement unit 11 as a sensor that senses a location of a pupil 15 in order to determine an eye motion of the user and includes a laser emitting unit and a laser receiving unit preferably irradiates an infrared laser in a wavelength band without vision damage of the pupil. In FIG. 2a, a laser irradiation line (LL) irradiated from the distance measurement unit 11 is illustrated for convenience of description.

Referring to FIG. 4, the plurality of distance measurement units 11 may irradiate infrared rays to an eyeball 10, and then measure a distance (d1+d2) in which the infrared rays are reflected on a fundus of the eyeball through the pupil 15 or a distance (d2) in which the infrared rays are directly reflected on a surface of the eyeball. That is, the reflection distance may be divided into a distance d1 from the fundus up to the eyeball surface (or pupil) and a distance d2 from the eyeball surface up to the sensor unit 114. In this case, a location of the pupil is sensed by measuring the respective distances d1 and d2 acquired through a plurality of sensors.

Specifically, laser beams irradiated from some distance measurement units 11 of the user pass through the pupil 15, and then are reflected in the fundus which is an inner side of the eyeball 10 of the user and sensed by the distance measurement unit 11 through the pupil 15 again.

In this case, only some of a plurality of laser beams irradiated from the plurality of distance measurement units 11 may pass through the pupil. A laser beam which does not pass through the pupil is reflected on the surface other than an inner part of the eyeball 10 and incident in the light receiving unit of the distance measurement unit 11.

The distance d1 from the fundus up to the eyeball surface and the distance d2 from the eyeball surface 10 up to the display unit 103 may be measured by using the lasers irradiated from the plurality of distance measurement units 11. That is, since the distance (d1+d2) in which the laser passes through the pupil 15 has a relatively shorter length than a distance (d1+d2) in which the laser does not pass through the pupil 15, the location of the user pupil 15 may be determined through comparing the lengths. Further, based on whether the laser beam irradiated from one distance measurement unit 11 passing through the pupil and/or a distance measured in the beam which passes through the pupil according to distance information of the plurality of distance measurement units 11, a direction which the pupil faces in the eyeball may be accurately determined.

Accordingly, according to the present invention, as illustrated in FIG. 4, since distances up to the fundus from various locations at which the plurality of distance measurement units 11 are positioned are measured, it is possible to derive a very detailed eye direction.

In this case, the plurality of distance measurement units 11 are arranged along an upper side L1 and a lower side L2 of a rear surface (a surface facing a face) of a support (glasses frame) supporting the display unit 103 of the smart glasses display device 100. However, the location of the distance measurement unit 11 is not limited thereto, and the distance measurement unit 11 may be arranged on a side portion of the rear surface of the glasses frame of the eye detection based smart glasses display device 100 or directly arranged on the lens 111 or the panel 112 of the display unit 103 of the smart glasses display device 100.

The eye detection unit 102 as a component that senses the eye direction of the user for an augmented reality image to be displayed on the display unit 103 may detect the eye direction based on the distance (d1+d2) in which the laser beam is reflected on the fundus of the eyeball through the pupil, the distance d2 in which the laser beam is directly reflected on the surface of the eyeball, and the location of the pupil. A more detailed description of the pupil sensing unit 101 and the eye detection unit 102 will be described below with reference to FIGS. 3a and 3b.

The display unit 103 is a component that displays the image acquired from the eye contact object 200 in the display unit 103 as an augmented reality, virtual reality or mixed reality image. For example, referring to FIG. 2b, the display unit 103 may include the microdisplay 10, the lens 111, the panel 112, and the splitter 13. In this case, when the microdisplay 10 irradiates the image through the lens 111 disposed on a front thereof, the irradiated image reaches one area of the panel 112 through the lens 111, and then the image may be totally reflected by a splitter 13 attached on one surface of the display panel 12 and the image 114 may be shown to the eyes of the user by the splitter 13 in front of the eye again.

Further, the display unit 103 may display the image or video acquired by the image acquisition unit 205 as the augmented reality, virtual reality, or mixed reality image, and display various information related to the acquired image. For example, when the medical team cuts a blood vessel of the patient upon the surgery, a remaining time up to safely connecting the blood vessel being approximately 60 seconds may be displayed as a second image 220 while being overlapped with the first image 210.

The augmented reality, virtual reality, or mixed image (hereinafter, referred to as the overlay image) acquired by the image acquisition unit 205, e.g., an image scanned by the ultrasonic scanner is overlaid with a specific location designated according to the eye contact object 200 through the display unit 103. For example, the image acquired by the image acquisition unit 205 may be an ultrasonic image of a maternity that takes an ultrasonic examination. In this case, the smart glasses display device 100 recognizes whether the eye contact object 200 (the ultrasonic scanner in the embodiment of FIG. 4) is within a specific range 250 from the eye direction. In addition, the overlay image acquired by the image acquisition unit 205 is overlaid with a specific location (e.g., in the case of the ultrasonic scanner, an ultrasonic wave irradiation surface of the ultrasonic scanner) depending on the eye contact object 200.

The image is displayed on a left lens and a right lens of the eye detection based smart glasses display device 100. In this case, the left lens and/or the right lens may display the same image. As illustrated in FIG. 1B, in respect to the image, a left-eye image T1' and a right-eye image T1' for the same object are displayed, and as a result, the user may also recognize a virtual object T1 as a stereoscopic shape (3D).

Further, the image may move within the display unit 103 based on the eye motion of the user. A detailed description related thereto will be described later.

The screen synthesis unit 104 may arrange and synthesize the image or video acquired by the image acquisition unit 205 at an appropriate location. The screen synthesis unit 104 computes checks the location of the eye contact object 200 through the image acquired by the external camera 12, and computes a location at which the overlay image is to be displayed in link with the eye direction. In the ultrasonic scanner embodiment of FIG. 4, the location at which the overlay image is to be displayed is the ultrasonic wave irradiation surface of the ultrasonic scanner. The screen synthesis unit 104 may control the display unit 103 to display the ultrasonic image at the computed location. In this case, the doctor may also check the scanned screen to be normally displayed while viewing the ultrasonic wave irradiation surface when scanning a stomach of the maternity through ultrasonic waves. Accordingly, the doctor may perform the ultrasonic examination while adjusting a location of a fetus and a desired portion to be normally scanned without dispersing the eye.

When the smart glasses display device 100 is the HMD which displays virtual reality, the screen synthesis unit 104 may overlap and display the image of the external camera 12 and the image of the image acquisition unit 205. However, even in this case, the location at which the overlay image is to be displayed is computed in link with the eye direction, and then the image of the external camera 12 and the image of the image acquisition unit 205 are overlaid and displayed.

The control unit 105 may perform a function of controlling all operations for the pupil sensing unit 101, the eye detection unit 102, the display unit 103, and the screen synthesis unit 104.

Hereinafter, a method for correcting a distance which the screen synthesis unit 104 estimates from the location of the pupil and the measured distances d1 and d2 will be described in detail with reference to FIGS. 3a and 3b.

Specifically, as illustrated in FIG. 3a, the screen synthesis unit 104 provides an arbitrary screen 300 displaying a circular guide area TR to the user through the display unit 103 in a calibration mode. Here, the calibration mode is a mode of measuring the eye direction of the user. The user is guided to move the eye in a clockwise direction (based on the user, on the other hand, may be a counterclockwise direction) along a periphery of the guide area (TR) at an initial start point (SP) along the guide area (TR) displayed in the arbitrary screen 300.

In this case, when the user moves the eye direction along the guide area (TR), the eye detection unit 102 detects the eye direction of the user. In this case, as illustrated in FIG. 3b, an ideal user eye has an ideal circular orbit, but an actual user eye is formed to have an elliptical orbit having a smaller horizontal width and a larger vertical width than the ideal user eye. In other words, an eye direction at which the user may conveniently stare generally has an elliptical shape other than an accurate circular shape. In this case, the screen synthesis unit 104 acquires an eye correction reference value based on the actual eye direction measured in the calibration mode. In this case, the eye correction reference value may include, for example, values which may represent an ellipse such as eccentricity, flatness, a focal location of the ellipse, etc.

Accordingly, the smart glasses display device 100 according to the present invention may correct the eye direction detected by the eye detection unit 102 based on the eye correction reference value. Accordingly, an eye direction which the user intends to actually view may be accurately estimated, and accuracy of a display location of the overlay image is remarkably increased in screen processing.

In the embodiment, the location of the eye contact object 200 is determined based on the image acquired through the external camera 12, but the present invention is not limited thereto. For example, the screen synthesis unit 104 may also determine the location of the eye contact object 200 by using beacons 260 mounted on at least three locations of the eye contact object 200. That is, the screen synthesis unit 104 may determine the location of the eye contact object 200 by periodically detecting signals of the beacons 260 mounted on the eye contact object 200.

Hereinafter, another embodiment according to the present invention will be described with reference to FIG. 5.

Figure 5:
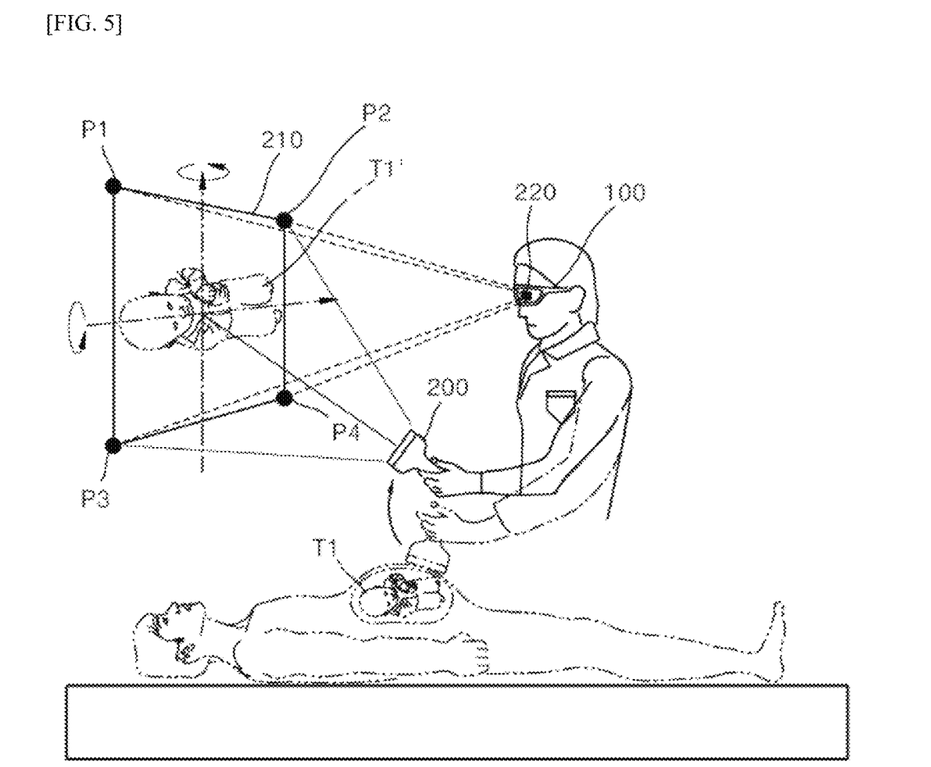
FIG. 5 is a diagram illustrating a smart glasses display method according to another embodiment of the present invention.

In the embodiment of FIG. 5, the eye contact object 200 may be light irradiated by a light irradiation unit 260 mounted on one surface of the ultrasonic scanner. For example, when the doctor desires to view an entire ultrasonic image at a desired location while performing the examination through the ultrasonic scanner, the doctor displays the desired location by turning on the light irradiation unit 260 mounted on the ultrasonic scanner.

In this case, when the light irradiated by the light irradiation unit 260 is sensed through the external camera 12, screen boundary points P1 to P4 and P2 to P3 are computed around a point to which the light is irradiated as illustrated in FIG. 5. Here, when it is assumed that a point to which an infrared laser is irradiated is a reference point, four points P1, P2, P3, and P4 spaced apart from each other by a predetermined interval in a diagonal direction around the reference point may be extracted as the screen boundary points. As a result, the screen synthesis unit 104 may compute the location of the overlay image 210 based on the light irradiated by the light irradiation unit 260 which is the eye contract object 200.

Meanwhile, FIG. 2*a* is an embodiment, and some components may be deleted or a new component may be added according to the need of those skilled in the art. For example, a controller connected to the eye detection based smart glasses display device 100 wirelessly/wiredly may also be further included.

Hereinafter, yet another embodiment according to the present invention will be described with reference to FIG. 6.

Figure 6:
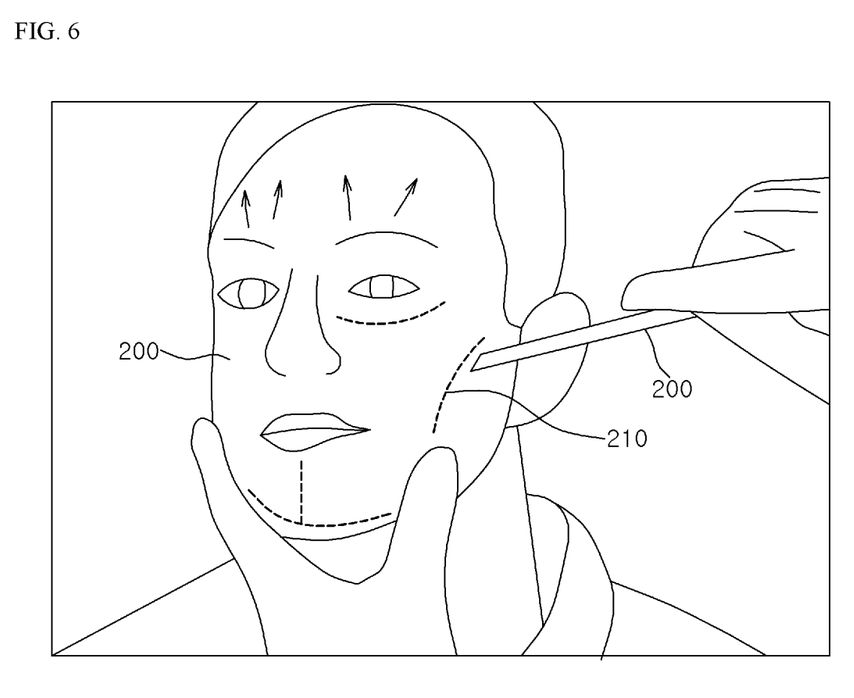
FIG. 6 is a diagram illustrating a smart glasses display method according to another embodiment of the present invention.

In the embodiment of FIG. 6, the eye contract object 200 may be the mes and a face of a surgery subject. Further, in this case, the overlay image 210 may be a scheduled surgery line. For example, when the doctor conducts a surgery that cuts the face of the patient by lifting the mes, a surgery line image may be overlaid with the face of the patient. In this case, when the face of the patient and the mes are detected in the image photographed by the external camera 12 within a predetermined range of the eye direction of a surgeon, the surgery line which is the overlay image is overlaid and displayed on the face of the patient. That is, there may be a plurality of eye contact objects 200, and when various conditions (when at least a part of the mes and the face of the surgery subject are detected) are satisfied, the screen synthesis unit 104 may compute the location of the overlay image 210 based on the face of the surgery subject which is the eye contract object 200. Alternatively, in this case, the overlay image 210 may also become information on a situation (information on whether a depth at which a surgery mes is inserted into a skin being appropriate) for reference. Alternatively, a location of a nerve/blood vessel which should not absolutely be touched upon the surgery may also be displayed as the overlay image 210. In this case, the overlaid overlay image 210 may be displayed by an existing known video processing method including a block search of the video or an edge detection scheme.

Accordingly, according to the present invention, the overlay image which moves based on the eye direction is displayed in a specific area of the smart glasses to allow the medical team to concentrate on an inborn task such as the surgery or the examination without dispersing the eye of the medical team.

Figure 7:
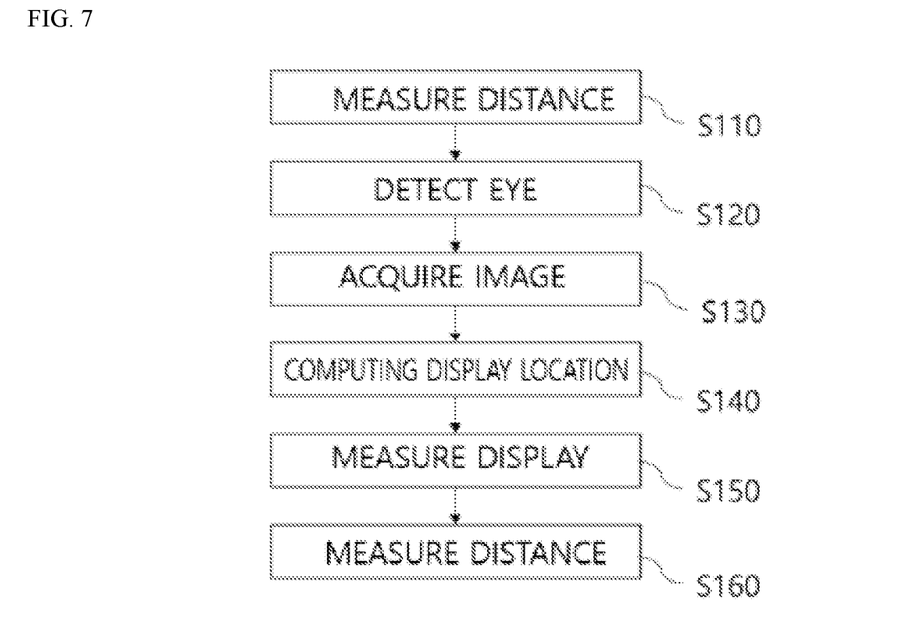
FIG. 7 is a diagram illustrating a smart glasses display method according to an embodiment of the present invention.

Hereinafter, an eye detection based smart glasses display method according to an embodiment of the present invention will be described in detail with reference to FIG. 7.

First, the smart glasses display method according to the embodiment of the present invention includes a distance measuring step (S110) of measuring a first distance from a fundus and a second distance from a surface of an eyeball by irradiating a laser to the eyeball including the fundus by a plurality of distance measurement units 11.

In this case, the eye detection unit 102 may detect the eye direction based on whether the distance measured by each distance measurement unit 11 being reflected from the fundus or reflected on the eyeball surface, i.e., the first distance and the second distance (eye detecting step, S120).

Meanwhile, the smart glasses display method acquires an overlay image. The overlay image may be acquired from an ultrasonic scanner, an external camera, a separate connected camera, or a server storing an image/video as described above (image acquisition step, S130). In this case, the eye detection unit 102 may sense a location of a pupil based on information on whether the distance measured by each of the plurality of distance measurement units being the first distance or the second distance. Alternatively, the eye detection unit 102 may detect the eye direction by sensing a direction which the pupil faces in the eyeball by the first distance measured by some distance measurement units among the plurality of distance measurement units.

The screen synthesis unit 104 may recognize an eye contact object within a predetermined range in the eye direction, and compute a location so as to display the overlay image at a designated location according to the eye contact object (display location computing step, S140). In this case, the screen synthesis unit 104 may provide a screen including a circular guide area by the display unit 103, and then detect the eye direction of a user and acquire an eye correction reference value based on an eye direction detected along a guide area when the user moves the eye along the provided guide area.

Meanwhile, the display location computing step (S140) may include a step of sensing light irradiated by the eye contact object and extracting a reference point for displaying the overlay image. In this case, the display location computing step may further include a step of extracting a point spaced apart from the reference point by a predetermined interval as a screen boundary point.

Last, the smart glasses display method may include a display step of displaying the overlay image at the computed location by a smart glasses type display unit 103. Accordingly, the present invention can provide a device which can display required information without dispersing an eye of a doctor at a time and a point desired by a doctor by using VR, AR, and MR.

Further, according to the present invention, there is an effect that an augmented reality image which moves based on an eye motion is displayed in a specific area which the user intuitively conveniently feels to allow the user to concentratively determine a diseased part or an inner part of a body of a patient through a virtual object without gaze dispersion.

Although the embodiments of the present invention have been described in detail with reference to the accompanying drawings, the present invention is not limited thereto and may be embodied in many different forms without departing from the technical concept of the present invention. Therefore, the embodiments of the present invention are provided for illustrative purposes only but not intended to limit the technical concept of the present invention. The scope of the technical concept of the present invention is not limited to the embodiment. Therefore, it should be understood that the above-described embodiments are illustrative in all aspects and do not limit the present invention. The protective scope of the present invention should be construed based on the following claims, and all the technical concepts in the equivalent scope thereof should be construed as falling within the scope of the present invention.

The invention claimed is:

1. An eye detection based smart glasses display device comprising:
   a plurality of distance measurement units irradiating a laser to an eyeball including a fundus and measuring a first distance from the fundus and a second distance from a surface of the eyeball;
   an eye detection unit detecting an eye direction based on the first distance and the second distance;
   an image acquisition unit acquiring an overlay image;
   a screen synthesis unit recognizing an eye contact object within a predetermined range in the eye direction, and computing a location so as to display the overlay image at a designated location according to the eye contact object; and
   a display unit displaying the overlay image at the computed location and has a smart glasses type,
   wherein the display unit provides a screen including a circular guide area, and the screen synthesis unit detects the eye direction of a user and acquires an eye correction reference value based on the eye direction detected along the guide area when an eye moves along the circular guide area.

2. The eye detection based smart glasses display device of claim 1, wherein the eye detection unit senses a location of a pupil based on information on whether the distance measured by each of the plurality of distance measurement units being the first distance or the second distance.

3. The eye detection based smart glasses display device of claim 1, wherein the eye detection unit detects the eye direction by sensing a direction which a pupil faces in the eyeball by the first distance measured by some distance measurement units among the plurality of distance measurement units.

4. The eye detection based smart glasses display device of claim 1, wherein at least some of the plurality of distance measurement units are arranged along a support supporting the display unit.

5. The eye detection based smart glasses display device of claim 1, wherein the eye correction reference value includes eccentricity, flatness, or a focal location of an ellipse.

6. The eye detection based smart glasses display device of claim 1, wherein the screen synthesis unit senses light irradiated by the eye contact object and extracts a reference point for displaying the overlay image.

7. The eye detection based smart glasses display device of claim 6, wherein the screen synthesis unit extracts a point spaced apart from the reference point by a predetermined interval as a screen boundary point.

8. The eye detection based smart glasses display device of claim 1, wherein the display unit displays the overlay image in a three-dimensional (3D) stereoscopic shape.

9. The eye detection based smart glasses display device of claim 1, wherein the display unit includes a microdisplay, a lens, a panel, and a splitter.

10. An eye detection based smart glasses display method comprising:
    a distance measuring step of irradiating, by a plurality of distance measurement units, a laser to an eyeball including a fundus and measuring a first distance from the fundus and a second distance from a surface of the eyeball;
    providing, by a display unit, a screen including a circular guide area;
    detecting an eye direction of a user and acquiring an eye correction reference value based the eye direction detected along the guide area when an eye of the user moves along the circular guide area;
    an eye detecting step of detecting the eye direction based on the first distance and the second distance;
    an image acquiring step of acquiring an overlay image;
    a display location computing step of recognizing an eye contact object within a predetermined range in the eye direction, and computing a location so as to display the overlay image at a designated location according to the eye contact object; and
    a display step of displaying, by a display unit having a smart glasses type, the overlay image at the computed location.

11. The eye detection based smart glasses display method of claim 10, wherein in the eye detecting step, a location of a pupil is sensed based on information on whether the distance measured by each of the plurality of distance measurement units being the first distance or the second distance.

12. The eye detection based smart glasses display method of claim 11, wherein in the eye detecting step, the eye direction is detected by sensing a direction which a pupil faces in the eyeball by the first distance measured by some distance measurement units among the plurality of distance measurement units.

13. The eye detection based smart glasses display method of claim 10, further comprising:
    the eye correction reference value includes eccentricity, flatness, or a focal location of an ellipse.

14. The eye detection based smart glasses display method of claim 10, wherein the display location computing step includes sensing light irradiated by the eye contact object and extracting a reference point for displaying the overlay image.

15. The eye detection based smart glasses display method of claim 14, wherein the display location computing step further includes extracting a point spaced apart from the reference point by a predetermined interval as a screen boundary point.

16. The eye detection based smart glasses display method of claim 10, wherein the display step includes displaying the overlay image in a three-dimensional (3D) stereoscopic shape.

17. A non-transitory computer readable recording medium storing instructions, wherein the instructions comprising:
- irradiating, by a plurality of distance measurement units, a laser to an eyeball including a fundus and measuring a first distance from the fundus and a second distance from a surface of the eyeball;
- providing, by a display unit, a screen including a circular guide area;
- detecting an eye direction of a user and acquiring an eye correction reference value based the eye direction detected along the guide area when an eye of the user moves along the circular guide area;
- detecting the eye direction based on the first distance and the second distance and acquiring an overlay image;
- recognizing an eye contact object within a predetermined range in the eye direction;
- computing a location so as to display the overlay image at a designated location according the eye contact object;
- displaying, by the display unit having a smart glasses type, the overlay image at the computed location.

* * * * *